United States Patent
Hirama et al.

(10) Patent No.: US 11,723,872 B2
(45) Date of Patent: *Aug. 15, 2023

(54) GRANULATED COMPOSITE, RAPID RELEASE TABLET AND METHOD FOR PRODUCING SAME

(71) Applicant: Shin-Etsu Chemical Co., Ltd., Tokyo (JP)

(72) Inventors: Yasuyuki Hirama, Joetsu (JP); Naosuke Maruyama, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 50 days.

This patent is subject to a terminal disclaimer.

(21) Appl. No.: 16/601,270

(22) Filed: Oct. 14, 2019

(65) Prior Publication Data

US 2020/0038333 A1 Feb. 6, 2020

Related U.S. Application Data

(62) Division of application No. 14/534,337, filed on Nov. 6, 2014, now abandoned.

(30) Foreign Application Priority Data

Nov. 15, 2013 (JP) ................. 2013-237000

(51) Int. Cl.
| | | |
|---|---|---|
| A61K 9/20 | (2006.01) | |
| A61K 9/16 | (2006.01) | |
| A61K 9/00 | (2006.01) | |
| A61K 31/166 | (2006.01) | |

(52) U.S. Cl.
CPC .......... *A61K 9/2054* (2013.01); *A61K 9/0056* (2013.01); *A61K 9/1623* (2013.01); *A61K 9/1635* (2013.01); *A61K 9/1652* (2013.01); *A61K 9/1694* (2013.01); *A61K 9/2018* (2013.01); *A61K 9/2027* (2013.01); *A61K 9/2095* (2013.01); *A61K 31/166* (2013.01)

(58) Field of Classification Search
CPC .. A61K 9/2095; A61K 9/2018; A61K 9/1694; A61K 9/1623; A61K 9/2054
See application file for complete search history.

(56) References Cited

U.S. PATENT DOCUMENTS

| | | |
|---|---|---|
| 3,864,406 A | 2/1975 | Melaja et al. |
| 8,303,868 B2 | 11/2012 | Maruyama |
| 8,303,869 B2 | 11/2012 | Magario et al. |
| 2002/0058714 A1 | 5/2002 | Maruyama |
| 2009/0110737 A1 | 4/2009 | Toda et al. |
| 2010/0187706 A1 | 7/2010 | Maruyama |
| 2011/0229570 A1* | 9/2011 | Sugimoto ............... A61P 19/06 424/465 |

FOREIGN PATENT DOCUMENTS

| | | | |
|---|---|---|---|
| EP | 1192942 | 4/2002 | |
| EP | 1260215 | 11/2002 | |
| EP | 2210591 | 7/2010 | |
| EP | 2465495 | 6/2012 | |
| EP | 2674149 | 12/2013 | |
| JP | 2008528442 | 7/2008 | |
| JP | 2012031138 | 2/2012 | |
| JP | 2010189384 | 9/2012 | |
| JP | 2012236823 | 12/2012 | |
| JP | 5876418 | 3/2016 | |
| WO | 2010061846 | 6/2010 | |
| WO | 2012091049 | 7/2012 | |
| WO | 2013058409 | 4/2013 | |
| WO | WO-2013098576 A1 * | 7/2013 | ........... A61K 9/2054 |

OTHER PUBLICATIONS

Liang et al.; "The Study of Formation of a Small Amount of Sorbitol in Bulk Drug Mannitol"; 2007; Journal of Mathematical Medicine; 20(6); 854-857 (Year: 2007).*

Rajniak et al.; "Experimental study of wet granulation in fluidized bed: Impact of the binder properties on the granule morphology"; 2007; International Journal of Pharmaceutics; 224:92-102; doi:10.1016/j.ijpharm.2006.10.040 (Year: 2007).*

"Industrial Pharmacy", Weisan Pan, Higher Education Press (2006) (with concise explanation of relevance).

European Pharmacopoeia Commission; "Mannitol"; 2008; Monograph No. 559; http://www.pharmacopoeia.gov.uk/custom/dormantmonographs/Mannitoi%20(2)%20-%20CRB.pdf, accessed Jun. 24, 2015.

Examination report under sections 12 & 13 of the Patents Act, 1970 and the Patents Rules, 2003, Application No. 3239/DEL/2014, Feb. 19, 2019,5 pp.

Extended European Search Report Corresponding to European Application No. 14192872.1: dated Mar. 19, 2015; 6 Pages.

Guyot-Hermann et al.; "Gamma Sorbitol as a Diluent in Tablets"; 1985; Drug Development and Industrial Pharmacy; 11(2&3):551-564.

(Continued)

*Primary Examiner* — Timothy P Thomas
(74) *Attorney, Agent, or Firm* — Myers Bigel, P.A.

(57) ABSTRACT

Provided is a rapid release tablet excellent in binding capability and disintegrability and also excellent in storage stability and the like. More specifically, provided are a granulated composite comprising low-substituted hydroxypropyl cellulose having a degree of hydroxypropoxy substitution of from 5 to 16% by weight and D-mannitol, wherein the D-mannitol contains 0.9% by weight or less of D-sorbitol; a rapid release tablet comprising the granulated composite and a drug; and a method for producing a granulated composite comprising the steps of: mixing low-substituted hydroxypropyl cellulose having a degree of hydroxypropoxy substitution of from 5 to 16% by weight, first D-mannitol, and water to obtain an aqueous dispersion, and granulating while adding the aqueous dispersion to second D-mannitol, wherein the first D-mannitol and the second D-mannitol contain 0.9% by weight or less of D-sorbitol in total.

3 Claims, No Drawings

(56) References Cited

OTHER PUBLICATIONS

Jivraj et al.; "An overview of the different excipients useful for the direct compression of tablets"; 2000: PSTT; 3(2):58-63.
Liang et al. "The Study of Formation of a Small Amount of Sorbitol in Bulk Drug Mannitol", J Mathematical Medicine 20(6):854-857 (2007) (with concise explanation of relevance).
Office Action corresponding to Chinese Application No. 201410648049.8 dated June 4, 2018.
Office Action corresponding to Japanese Application No. 2014-231521 dated Oct. 17, 2017.
Partial Translation of Dictionary of Pharmaceutical Additives, p. 77 (1994).

* cited by examiner

GRANULATED COMPOSITE, RAPID RELEASE TABLET AND METHOD FOR PRODUCING SAME

RELATED APPLICATION

This application is a divisional of U.S. patent application Ser. No. 14/534,337, filed Nov. 6, 2014, which claims priority from Japanese Patent Application No. 2013-237000, filed Nov. 15, 2013, the disclosures of which are incorporated by reference herein in their entirety.

FIELD AND BACKGROUND OF THE INVENTION

The present invention relates to a granulated composite and a rapid release tablet, each comprising low-substituted hydroxypropyl cellulose, which are used in the field of pharmaceuticals, food or the like; and a method for producing them.

In recent years, there has been a demand for the development of orally rapidly disintegrating tablet which a patient having low swallowing ability, such as the aged or an infant, can take easily without water. The orally rapidly disintegrating tablet is not limited to a patient having low swallowing ability, but is convenient and useful for any patient since it is in dosage form taken without water.

The orally rapidly disintegrating tablet is required to have a short disintegration time in the oral cavity and a tablet hardness enough to withstand breakage during production or transport. In addition, since the orally rapidly disintegrating tablet sometimes has a reduced hardness and a prolonged disintegration time owing to moisture absorbed thereby when exposed to a humidified environment after opening, it is desired in a medical site that the orally rapidly disintegrating tablet have excellent storage stability, allowing the tablet after opening to have the tablet hardness as high as and a disintegration time as short as those immediately after production.

As a method for producing an orally rapidly disintegrating tablet, there are known a freeze-drying method, a thermal tableting method and the like. These methods need a special apparatus because typical compression molding equipment for drug production is not suited for them. There is therefore a demand for the development of a method for producing an orally rapidly disintegrating tablet without using a special technology or apparatus. Direct dry-tableting has recently attracted attentions as a method for producing an orally rapidly disintegrating tablet. The direct dry-tableting is a method comprising the steps of simply mixing a drug and an additive, further mixing in addition of a lubricant, and then compression-molding the resulting mixture into tablets. This method is productive because it needs neither a special technology nor a special apparatus and further, it comprises neither a granulation step nor a drying step.

JP 2010-189384A discloses a granulation method using a sugar or sugar alcohol and an aqueous dispersion of low-substituted hydroxypropyl cellulose.

SUMMARY OF THE INVENTION

The orally rapidly disintegrating tablet obtained in the method of JP 2010-189384A is excellent in disintegrability but further improvement in moldability is desired. In addition, the disintegration time sometimes increases during storage so that further improved storage stability is desired.

With the foregoing in view, the invention has been made. An object is to provide a granulated composite and a rapid release tablet excellent in binding capability and disintegrability and also excellent in storage stability.

The present inventors have studied a granulated composite comprising low-substituted hydroxypropyl cellulose and D-mannitol. As a result, it has been found unexpectedly that an orally disintegrating tablet comprising a drug and a granulated composite comprising low-substituted hydroxypropyl cellulose and D-mannitol having small D-sorbitol content is excellent in disintegrability and also excellent in storage stability, leading to the completion of the invention.

In one aspect of the invention, there is provided a granulated composite comprising low-substituted hydroxypropyl cellulose having a degree of hydroxypropoxy substitution of from 5 to 16% by weight and D-mannitol, wherein the D-mannitol contains 0.9% by weight or less of D-sorbitol. In another aspect, there is provided a rapid release tablet comprising the granulated composite and a drug. In a further aspect of the invention, there is provided a method for producing a granulated composite comprising the steps of: mixing low-substituted hydroxypropyl cellulose having a degree of hydroxypropoxy substitution of from 5 to 16% by weight, first D-mannitol and water to obtain an aqueous dispersion, and granulating while adding the aqueous dispersion to second D-mannitol, wherein the first and the second D-mannitol contain 0.9% by weight or less of D-sorbitol. In a still further aspect of the invention, there is provided a method for producing a rapid release tablet comprising each step comprised by the method for producing the granulated composite, a step of mixing the granulated composite with a drug to obtain a mixture, and a step of tableting the mixture.

According to the invention, the granulated composite can provide a rapid release tablet having high hardness and excellent disintegrability, free of reduction in hardness and increase in disintegration time under humidified conditions, and excellent in storage stability, without using a special method or special apparatus. Accordingly, a tablet which can be taken smoothly and handled easily can be produced with respect to oral administration of the tablet comprising a various type of drug in the field of pharmaceuticals, food or the like. According to the invention, the granulated composite is nonionic and has low hygroscopicity so that it has less interaction with a drug and is suited for production of rapid release tablet excellent in stability.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

D-mannitol is usually produced by hydrogenating easily available fructose as a raw material. Since hydrogenation of fructose is not stereoscopic, it produces D-mannitol and sorbitol in almost equal amounts. After the hydrogenation, therefore, D-mannitol is separated and purified in another step and then provided as a product.

D-mannitol is now produced by a plurality of manufacturers and its purification degree varies depending on a manufacturer. Even D-mannitol produced by the same manufacturer sometimes has a different degree of purification.

With a view to achieving the above-mentioned object, the present inventors have carried out an intensive investigation and have focused on the content of D-sorbitol slightly present as an impurity in D-mannitol which is one of sugar alcohols.

The D-sorbitol content in D-mannitol comprised by the granulated composite is less than 0.9% by weight, preferably 0.3% by weight or less. When the content is more than 0.9% by weight, a disintegration time increases during storage of the rapid release tablet comprising the granulated composite and a drug.

The D-sorbitol content in D-mannitol can be measured using the method of liquid chromatography described in the section of D-mannitol in EUROPEAN PHARMACOPOEIA 7.5. For example, it can be measured under the conditions of a feed rate of 0.5 mL/min and a column oven temperature of 85° C. while using Rezex RCM-Monosaccharide $Ca^{2+}$ (8%) 300×8 mm (product of Phenomenex) as a column, RID (differential refractive index detector) as a detector, and ultrapure water as a mobile phase.

According to the invention, the granulated composition can be produced by granulation while adding an aqueous dispersion prepared by mixing low-substituted hydroxypropyl cellulose, first D-mannitol and water to second D-mannitol.

It should be noted that the D-sorbitol content in the D-mannitol contained by the granulated composite is a sum of first D-sorbitol content in the first D-mannitol contained by the aqueous dispersion and second D-sorbitol content in the second D-mannitol to which the aqueous dispersion is added.

The average particle size of the first D-mannitol to be dissolved in water is not particularly limited insofar as it is soluble therein. It is preferably from 5 to 500 μm, more preferably from 10 to 100 μm. D-mannitol having an average particle size of less than 5 μm is not easily available industrially. D-mannitol having an average particle size of more than 500 μm may result in lowered disintegrability and binding capability because of the presence of undissolved portion.

The average particle size of the second D-mannitol to which the aqueous dispersion is added is preferably from 5 to 200 μm, more preferably from 5 to 100 μm, still more preferably from 10 to 50 μm. When the average particle size is less than 5 μm, fluidity or disintegrability may be lowered. When it is more than 100 μm, binding capability may be lowered.

The average particle size of each of the first D-mannitol and the second D-mannitol is a volume-based particle size and can be measured by a powder size measurement method using laser diffraction. It can be measured using, for example, HELOS & RODOS (product of Japan Laser Corp.).

A total amount of the first D-mannitol comprised by the aqueous dispersion and the second D-mannitol to which the aqueous dispersion is added is preferably from 80 to 99% by weight, more preferably from 90 to 98% by weight, in the resulting granulated composite. When the total amount is less than by weight, texture in the oral cavity may be lowered, or the stability of the drug formulation may be lowered owing to increased hygroscopicity caused by an increase in the amount of the other additive. When the total amount is more than 99% by weight, the intended binding capability or disintegrabilty may not be obtained.

The amount of the first D-mannitol comprised by the aqueous dispersion is preferably from 1 to 50% by weight, more preferably from 5 to 30% by weight in the total amount of the D-mannitol comprised by the granulated composite obtained. When the amount is less than 1% by weight, binding capability or disintegrability may be lowered. When the amount is more than 50% by weight, an undissolved portion may become large, or may precipitate or cause clogging during feeding.

The low-substituted hydroxypropyl cellulose is a water-insoluble polymer and swells by water absorption. It has a basic cellulose skeleton and contains a small amount of hydroxypropoxy groups introduced therein. It has the degree of hydroxypropoxy substitution of from 5 to 16% by weight, more preferably from 5 to 9% by weight. When the degree of hydroxypropoxy substitution is less than 5% by weight, the swelling property by water absorption is low so that the intended disintegrability is not obtained, and the binding capability is also lowered. When the degree of hydroxypropoxy substitution is more than 16% by weight, water solubility increases, the intended disintegrability is not obtained, and the disintegration time of tablets obtained by molding prolongs, in spite of increase in swelling property and improvement in binding capability. The degree of hydroxypropoxy substitution is measured using a method described in "low-substituted hydroxypropyl cellulose" of The Japanese Pharmacopoeia, Sixteenth Edition.

The average particle size of the low-substituted hydroxypropyl cellulose is preferably from 5 to 100 μm, more preferably from 10 to 80 still more preferably from 20 to 60 μm. When the average particle size is less than 5 μm, swelling by water absorption may be lowered so that disintegrability may be lowered. When the average particle size is more than 100 μm, binding capability may be lowered owing to reduction in specific surface area. It should be noted that the average particle size is a volume-based average particle size and can be measured by a powder size measuring method using laser diffraction. It can be measured using, for example, HELOS & RODOS (product of Japan Laser Corp).

The amount of the low-substituted hydroxypropyl cellulose is preferably from 1 to 20% by weight, more preferably from 2 to 10% by weight in the granulated composite obtained. When the amount is less than 1% by weight, a tablet having the intended disintegrability may not be obtained. When the amount is more than 20% by weight, an increase in the amount of water-insoluble substance may deteriorate the texture in the oral cavity, and enhanced hygroscopicity may lower the stability of the drug formulation thus obtained.

The aqueous dispersion preferably further comprises polyvinyl alcohol from the standpoint of the binding capability. The amount of the polyvinyl alcohol is preferably from 0.05 to 0.4% by weight, more preferably from 0.1 to 0.3% by weight in the granulated composite thus obtained. When the amount is less than 0.05% by weight, the binding capability may not reach an intended level. When the amount is more than 0.4% by weight, the disintegrability may be lowered although the binding capability is excellent.

Polyvinyl alcohol is a water-soluble polymer and is used as a binder. It can be prepared by polymerization of vinyl acetate monomer and then saponification with an alkali. The polyvinyl alcohol is classified depending on the saponification degree. Polyvinyl alcohol having a saponification degree of from 80 to 90 mol %, polyvinyl alcohol having a saponification degree of more than 90 mol % but less than 98 mol %, and polyvinyl alcohol having a saponification degree of 98 mol % or greater are classified as "partially saponified type", "intermediately saponified type" and "fully saponified type", respectively. The partially saponified type polyvinyl alcohol dissolves in water of room temperature; the fully saponified type does not dissolve in water of room temperature but dissolves in water as hot as 90° C. or greater; and the intermediately saponified type shows a property between them.

The polyvinyl alcohol to be comprised by the aqueous dispersion is preferably a fully saponified type. The fully saponified type polyvinyl alcohol is rich in hydroxyl groups so that it improves the binding capability further due to many hydrogen bonds formed.

The polyvinyl alcohol has the polymerization degree of preferably from about 500 to 2000, which is commercially available.

The polymerization degree and saponification degree can each be measured based on JIS K6726.

Next, a method for producing a granulated composite will be described.

An aqueous dispersion comprising the low-substituted hydroxypropyl cellulose, D-mannitol and preferable optional polyvinyl alcohol may be prepared by dissolving the D-mannitol and the polyvinyl alcohol in a predetermined amount of water and then adding the low-substituted hydroxypropyl cellulose to the resulting solution, or inversely, adding the resulting solution to the low-substituted hydroxypropyl cellulose. The low-substituted hydroxypropyl cellulose is insoluble in water, and can be rapidly dispersed in water so that mixing for several minutes with a typical stirrer is sufficient. During granulating operation, the aqueous dispersion is preferably stirred in order to prevent precipitation.

The solid content in the aqueous dispersion is preferably from 1 to 30% by weight, more preferably from 5 to 25% by weight, still more preferably from 10 to 25% by weight. When the solid content is less than 1% by weight, productivity may be lowered because it takes long hours to complete the addition of a predetermined amount. When the solid content is more than 30% by weight, the aqueous dispersion may have excessively high viscosity and make feeding difficult. Herein, the solid content in the aqueous dispersion means a concentration of solids which can be obtained by drying the aqueous dispersion and which constitute a granulated composite.

According to the invention, an apparatus to be used in granulating operation includes a fluidized bed granulator, a stirring granulator, a tumbling fluidized bed granulator, and a spray drying granulator. It is preferably a fluidized bed granulator since it can perform spraying and drying simultaneously and easily forms a uniform coating layer on the powder surface.

The granulating operation will next be described with fluidized bed granulation as an example. Second D-mannitol is placed in a fluidized bed, and granulation is carried out while spraying, as a binder liquid, an aqueous dispersion which, for example, comprises low-substituted hydroxypropyl cellulose and first D-mannitol, to the second D-mannitol, thereby producing a granulated composite.

The average particle size of the granulated composite differs depending on the granulation conditions. It is preferably from 50 to 300 µm, more preferably from 50 to 250 µm, still more preferably from 50 to 200 µm. When the average particle size is less than 50 µm, the granulated composite may adhere to a tableting machine owing to low fluidity. When the average particle size is more than 300 µm, filling ability of the granulated composite into a mortar may be lowered so that the table weight variation may increase. The average particle size of the granulated composite can be measured using the sieving method described in the General Tests of the Japanese Pharmacopoeia, Sixteenth Edition.

When the dried granulated composite is obtained through a fluidized bed granulator capable of spraying and drying simultaneously, further drying is not necessary. If the granulated composite is obtained without drying or obtained using a granulator incapable of drying, then drying can be carried out in a known manner. For example, it can be dried at from 40 to 80° C. with a fluidized bed dryer or a shelf dryer. The water content of the granulated composite thus obtained is preferably 5% by weight or less, more preferably 1% by weight or less. When the water content is more than 5% by weight, the stability of a drug formulation may be adversely affected.

According to the invention, a rapid release tablet comprising the granulated composite thus obtained and a drug can be provided. The rapid release tablet means a tablet having a short disintegration time not only in the oral cavity but also in the stomach.

The production of a tablet by using the granulated composite will next be described, taking an example of the direct dry-tableting method. The granulated composite thus obtained are mixed with a drug to form a mixture, and then the mixture can be tableted through compression under a predetermined pressure with a typical continuous rotary press. The size of the tablet can be selected freely. The tablet preferably has a diameter of from about 6 to 12 mm and a weight of from 70 to 700 mg per tablet. When the tablet has a diameter of less than 6 mm, handling may not be easy. When the tablet has a diameter of more than 12 mm, swallowing the tablet may not be easy.

The tableting pressure is preferably from 10 to 300 MPa. When the tableting pressure is less than 10 MPa, the resulting tablet may not have an intended hardness. When the tableting pressure is more than 300 MPa, tableting troubles such as capping may happen.

According to the invention, a drug usable for a tablet comprising the granulated composite is not particularly limited insofar as it is orally administrable. Examples of the drug include a drug for the central nervous system, a drug for the circulatory system, a drug for the respiratory system, a drug for the digestive system, an antibiotic, an antitussive/expectorant, an antihistamine, an analgesic, antipyretic and anti-inflammatory drug, a diuretic, an autonomic drug, an antimalarial drug, an antidiarrheal agent, a psychotropic drug, and vitamins and derivatives thereof.

Examples of the drug for the central nervous system include diazepam, idebenone, aspirin, ibuprofen, paracetamol, naproxen, piroxicam, dichlofenac, indomethacin, sulindac, lorazepam, nitrazepam, phenytoin, acetaminophen, ethenzamide, ketoprofen and chlordiazepoxide.

Examples of the drug for the circulatory system include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, propranolol hydrochloride and alprenolol hydrochloride.

Examples of the drug for the respiratory system include amlexanox, dextromethorphan, theophilline, pseudo-ephedrine, salbutamol and guaiphenesin.

Examples of the drug for the digestive system include benzimidazole-based drugs having anti-ulcer action such as 2-[(3-methyl-4-(2,2,2-trifluoroethoxy)-2-pyridyl)methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl and 5-aminosalicylic acid.

Examples of the antibiotic include talampicillin hydrochloride, bacampicillin hydrochloride, cephaclor and erythromycin.

Examples of the antitussive/expectorant include noscapine hydrochloride, carbetapentane citrate, dextromethorphan hydrobromide, isoaminile citrate and dimemorfan phosphate.

Examples of the antihistamine include chlorpheniramine maleate, diphenhydramine hydrochloride and promethazine hydrochloride.

Examples of the analgesic, antipyretic and anti-inflammatory drug include ibuprofen, diclofenac sodium, flufenamic acid, sulpyrine, aspirin and ketoprofen.

Examples of the diuretic include caffeine.

Examples of the autonomic drug include dihydrocodeine phosphate, methylephedrine dl-hydrochloride, atropine sulfate, acetylcholine chloride and neostigmine.

Examples of the antimalarial drug include quinine hydrochloride.

Examples of the antidiarrheal agent include loperamide hydrochloride.

Examples of the psychotropic drug include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate and tranexamic acid.

According to the invention, the tablet may comprise, besides the granulated composite, an optional additive typically used in a solid preparation, together with a drug, wherein the additive may be in a typically used amount. Examples of such an additive include a disintegrant, a binder, a bulking agent, a lubricant, a taste corrigent and a flavor.

Examples of the disintegrant include low-substituted hydroxypropyl cellulose, corn starch, potato starch, partly pregelatinized starch, carboxymethyl starch sodium, carmellose, croscarmellose sodium, crystalline cellulose and crospovidone.

Examples of the binder include hydroxypropyl cellulose, polyvinylpyrrolidone and hydroxypropylmethyl cellulose.

Examples of the bulking agent include erythritol, D-mannitol, lactose, sucrose, calcium phosphate and calcium sulfate.

Examples of the taste corrigent include citric acid, tartaric acid and malic acid.

Examples of the flavor include menthol, peppermint oil and vanillin.

Examples of the lubricant include magnesium stearate and sucrose fatty acid ester.

The hardness of the tablet is preferably 40N or greater, more preferably 50N or greater immediately after production as well as after storage under humidified conditions. When the tablet hardness is less than 40N, breakage or cracks may be caused during transport or during packaging with an automatic packaging machine.

As the tablet hardness, maximum breaking strength at the time when the tablet is broken as a result of application of load at a rate of 1 mm/sec in a direction of the diameter of the tablet is measured. It can be measured using, for example, a tablet hardness tester ("TBH-30" product of ERWEKA).

The disintegration time of the tablet in the oral cavity is preferably within 30 seconds, more preferably within 20 seconds immediately after production as well as after storage under humidified conditions. When the disintegration time in the oral cavity is longer than 30 seconds, ease in taking the tablet may worsen.

The disintegration time in the oral cavity can be measured by administering the tablet to a human subject and allowing the tablet to disintegrate in her or his oral cavity in practice, but the disintegration time may vary largely depending on the subject. It is therefore measured using a disintegration tester for orally disintegrating tablets capable of measuring the oral disintegration time objectively. It can be measured using, for example, an orally rapid disintegrating tablet disintegration tester ("TRICORPTESTER", product of Okada Seiko Co., Ltd.).

D-mannitol is soluble in water, and inferior in compression moldability so that D-mannitol is apt to cause a tableting trouble such as capping. According to the invention, the granulated composite is not a mixture in which D-mannitol and low-substituted hydroxypropyl cellulose are physically mixed, but particles, each particle comprising the low-substituted hydroxypropyl cellulose on the surface of the D-mannitol.

According to the invention, both high binding capability and rapid disintegrability can be achieved by adding (preferably spraying) an aqueous dispersion comprising low-substituted hydroxypropyl cellulose, first D-mannitol and preferably optional polyvinyl alcohol to second D-mannitol so as to cover the surface of the second D-mannitol with the aqueous dispersion for surface modification. The reason why both the high binding capability and rapid disintegrability can be achieved is presumably because of the following reasons. The surface of the granulated composite is covered with the low-substituted hydroxypropyl cellulose and preferably optional polyvinyl alcohol, and the low-substituted hydroxypropyl cellulose and polyvinyl alcohol, both being rich in hydroxyl groups, can make firm hydrogen bonds during compression molding, thereby enhancing the binding capability. In addition, the low-substituted hydroxypropyl cellulose rapidly absorbs water and swells therewith so that the compression molded product disintegrates rapidly.

Further, according to the present invention, the rapid release tablet comprising the granulated composite and the drug is excellent in storage stability under humidified conditions. This means that reduction in hardness and prolongation of disintegration time hardly occur. The reason why the reduction in tablet hardness hardly occurs is presumably because the low-substituted hydroxypropyl cellulose has low hygroscopicity in comparison with the other disintegrants and does not easily cause swelling due to moisture absorption even under humidified conditions. The reason why prolongation of disintegration time hardly occurs is presumably because the D-sorbitol content in the D-mannitol comprised by the granulated composite is small. D-mannitol is a sugar alcohol having low hygroscopicity, while D-sorbitol is a sugar alcohol having high hygroscopicity. When the D-sorbitol content in the D-mannitol is large, D-sorbitol absorbs moisture under humidified conditions so that D-mannitol present in the vicinity of the D-sorbitol partially dissolves and consolidates to reduce the void area in the tablet. Consequently, water invasiveness is obstructed and prolongs the disintegration time. It is presumed that the lower the D-sorbitol content in D-mannitol is, the more the prolongation of the disintegration time can be suppressed.

EXAMPLES

The invention will hereinafter be described specifically by Examples and Comparative Examples. However, it should not be construed that the invention is limited to or by the following Examples.

Example 1

The 60.0 g of first D-mannitol having D-sorbitol content of 0.1% by weight was added to 322.0 g of purified water, and dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 222.0 g of second D-mannitol having D-sorbitol content of 0.1% by weight was placed in a fluidized bed granulator, and granulation was carried out by spraying the aqueous dispersion thereto at an intake air temperature of 80° C., an exhaust air temperature of from 34 to 37° C., a fluidizing air rate of from 0.5 to 0.7 m³/min, a spray rate of 15 g/min, and a spray air pressure of 125 kPa. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted at a tableting pressure of 7.5 kN with a rotary tableting machine into tablets, each tablet having a diameter of 8 mm, a radius of curvature of 12 mm and a tablet weight of 200 mg. Consequently, orally rapidly disintegrating tablets were produced.

The hardness and oral disintegration time of the tablets immediately after the production were measured by using a tablet hardness tester (TBH-30 produced by ERWEKA) and a disintegration testing apparatus for oral fast-disintegrating tablets (TRICORPTESTER produced by Okada Seiko Co., Ltd.), respectively. Further, the hardness and oral disintegration time of the tablets after storage for one week under the conditions of 40° C. and 75% RH (Relative Humidity) were measured again. The results are shown in Table 2.

Example 2

The 60.0 g of first D-mannitol having D-sorbitol content of 0.8% by weight was added to 322.0 g of purified water, and dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 222.0 g of second D-mannitol having D-sorbitol content of 0.8% by weight was placed in a fluidized bed granulator, and granulation was carried out by spraying the aqueous dispersion thereto in the same manner as in Example 1. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted in the same manner as in Example 1. The tablets thus obtained were evaluated in the same manner as in Example 1. The results are shown in Table 2.

Example 3

The 6.0 g of 10% by weight aqueous solution of polyvinyl alcohol having a saponification degree of 98.5% and a polymerization degree of 1700 and 60.0 g of first D-mannitol having D-sorbitol content of 0.1% by weight were added to 316.0 g of purified water, and dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 221.4 g of second D-mannitol having D-sorbitol content of 0.1% by weight was placed in a fluidized bed granulator, and granulation was carried out by spraying the resulting aqueous dispersion thereto in the same manner as in Example 1. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted at a tableting pressure of 5.0 kN with a rotary tableting machine into tablets, each tablet having a diameter of 8 mm, a radius of curvature of 12 mm and a tablet weight of 200 mg. Consequently, orally rapidly disintegrating tablets were produced. The tablets thus obtained were evaluated in the same manner as in Example 1. The results are shown in Table 2.

Example 4

The 6.0 g of 10% by weight aqueous solution of polyvinyl alcohol having a saponification degree of 98.5 mol % and a polymerization degree of 1700 and 60.0 g of first D-mannitol having D-sorbitol content of 1.0% by weight were added to 316.0 g of purified water, and dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 221.4 g of second D-mannitol having D-sorbitol content of 0.1% by weight was placed in a fluidized bed granulator, and granulation was carried out by spraying the aqueous dispersion thereto in the same manner as in Example 1. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted in the same manner as in Example 3. The tablets thus obtained were evaluated in the same manner as in Example 1. The results are shown in Table 2.

Example 5

The 6.0 g of 10% by weight aqueous solution of polyvinyl alcohol having a saponification degree of 98.5 mol % and a polymerization degree of 1700 and 60.0 g of first D-mannitol having D-sorbitol content of 0.3% by weight were added to 316.0 g of purified water, and dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 221.4 g of second D-mannitol having D-sorbitol content of 0.3% by weight was placed in a fluidized bed granulator, and granulation was carried out by spraying the aqueous dispersion thereto in the same manner as in Example 1. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted in the same manner as in Example 3. The tablets thus obtained were evaluated in the same manner as in Example 1. The results are shown in Table 2.

Example 6

The 6.0 g of 10% by weight aqueous solution of polyvinyl alcohol having a saponification degree of 98.5 mol % and a polymerization degree of 1700 and 60.0 g of first D-mannitol having D-sorbitol content of 0.1% by weight was added to 316.0 g of purified water, and dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 221.4 g of second D-mannitol having D-sorbitol content of 1.0% by weight was placed in a fluidized bed granulator, and granulation was carried out by spraying the aqueous dispersion thereto in the same manner as in Example 1. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted in the same manner as in Example 3. The tablets thus obtained were evaluated in the same manner as in Example 1. The results are shown in Table 2.

Example 7

The 6.0 g of 10% by weight aqueous solution of polyvinyl alcohol having a saponification degree of 98.5 mol % and a polymerization degree of 1700 and 60.0 g of first D-mannitol having D-sorbitol content of 0.8% by weight were added to 316.0 g of purified water, and then dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 221.4 g of second D-mannitol having D-sorbitol content of 0.8% by weight was placed in a fluidized bed granulator, and granulation was carried out by spraying the aqueous dispersion thereto in the same manner as in Example 1. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted in the same manner as in Example 3. The tablets thus obtained were evaluated in the same manner as in Example 1. The results are shown in Table 2.

Comparative Example 1

The 60.0 g of first D-mannitol having D-sorbitol content of 2.0% by weight was added to 322.0 g of purified water, and dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 222.0 g of second D-mannitol having D-sorbitol content of 2.0% by weight was placed in a fluidized bed granulator, and granulation was carried out by spraying the resulting aqueous dispersion thereto at an intake air temperature of 80° C., an exhaust air temperature of from 34 to 37° C., a fluidizing air rate of from 0.5 to 0.7 m³/min, a spray rate of 15 g/min, and a spray air pressure of 125 kPa. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted in the same manner as in Example 1. The tablets thus obtained were evaluated in the same manner as in Example 1. The results are shown in Table 2.

Comparative Example 2

The 6.0 g of 10% by weight aqueous solution of polyvinyl alcohol having a saponification degree of 98.5 mol % and a polymerization degree of 1700 and 60.0 g of first D-mannitol having D-sorbitol content of 1.0% by weight were added to 316.0 g of purified water, and dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 221.4 g of second D-mannitol having D-sorbitol content of 1.0% by weight was placed in a fluidized bed granulator, and granulation was carried out by spraying the resulting aqueous dispersion in the same manner as in Example 1. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted in the same manner as in Example 3. The tablets thus obtained were evaluated in the same manner as in Example 1. The results are shown in Table 2.

Comparative Example 3

The 6.0 g of 10% by weight aqueous solution of polyvinyl alcohol having a saponification degree of 98.5 mol % and a polymerization degree of 1700 and 60.0 g of first D-mannitol having D-sorbitol content of 2.0% by weight were added to 316.0 g of purified water, and dissolved by mixing with a stirring blade. Then 18.0 g of low-substituted hydroxypropyl cellulose having a degree of hydroxypropoxy substitution of 8% by weight was added to the resulting aqueous solution and mixed to produce an aqueous dispersion. Next, 221.4 g of second D-mannitol having D-sorbitol content of 2.0% by weight was placed in a fluidized bed granulator, and granulation was carried out by spraying the resulting aqueous dispersion thereto in the same manner as in Example 1. The composition of the aqueous dispersion and the composition of the granulated composite are shown in Table 1.

The 90 parts by weight of the granulated composite was mixed with 10 parts by weight of ethenzamide as a drug, and then 1.0 part by weight of magnesium stearate as a lubricant was added thereto and mixed. The resulting mixture was tableted in the same manner as in Example 3. The tablets thus obtained were evaluated in the same manner as in Example 1. The results are shown in Table 2.

In Comparative Example 1 where the D-mannitol comprised by the granulated composite had D-sorbitol content of greater than 0.9% by weight, the tablets immediately after the production showed an excellent disintegrability, but the disintegration time of the tablets after storage under humidified conditions increased. On the other hand, in Examples 1 and 2 where the D-sorbitol content in the D-mannitol comprised by the granulated composite was 0.9% by weight or less, the tablets immediately after the production as well as after storage under humidified conditions showed excellent binding capability and disintegrability, and were excellent in storage stability.

In Example 3 where the granulated composite further comprised polyvinyl alcohol differing from that in Example 1, the binding capability was increased so that the tablets having sufficient hardness were obtained even at a low tableting pressure. In addition, the tablets immediately after the production as well as after storage under humidified conditions showed excellent disintegrability and were excellent in storage stability. On the other hand, in Comparative Examples 2 and 3, the tablets immediately after production

TABLE 1

| | aqueous dispersion | | | | | powder to which aq. dispersion is added | | granulated composite | | | |
|---|---|---|---|---|---|---|---|---|---|---|---|
| | L-HPC (pbw) | MN (pbw) | PVA (pbw) | purified water (pbw) | S content in MN (wt %) | MN (pbw) | S content in MN (wt %) | L-HPC (pbw) | MN (pbw) | PVA (pbw) | S content in MN (wt %) |
| Example 1 | 6 | 20 | — | 107.3 | 0.1 | 74.0 | 0.1 | 6 | 94.0 | — | 0.10 |
| Example 2 | 6 | 20 | — | 107.3 | 0.8 | 74.0 | 0.8 | 6 | 94.0 | — | 0.80 |
| Example 3 | 6 | 20 | 0.2 | 107.1 | 0.1 | 73.8 | 0.1 | 6 | 93.8 | 0.2 | 0.10 |
| Example 4 | 6 | 20 | 0.2 | 107.1 | 1.0 | 73.8 | 0.1 | 6 | 93.8 | 0.2 | 0.29 |
| Example 5 | 6 | 20 | 0.2 | 107.1 | 0.3 | 73.8 | 0.3 | 6 | 93.8 | 0.2 | 0.30 |
| Example 6 | 6 | 20 | 0.2 | 107.1 | 0.1 | 73.8 | 1.0 | 6 | 93.8 | 0.2 | 0.81 |
| Example 7 | 6 | 20 | 0.2 | 107.1 | 0.8 | 73.8 | 0.8 | 6 | 93.8 | 0.2 | 0.80 |
| Comp. Ex. 1 | 6 | 20 | — | 107.3 | 2.0 | 74.0 | 2.0 | 6 | 94.0 | — | 2.00 |
| Comp. Ex. 2 | 6 | 20 | 0.2 | 107.1 | 1.0 | 73.8 | 1.0 | 6 | 93.8 | 0.2 | 1.00 |
| Comp. Ex. 3 | 6 | 20 | 0.2 | 107.1 | 2.0 | 73.8 | 2.0 | 6 | 93.8 | 0.2 | 2.00 |

* The abbreviations in Table 1 are as follows:
L-HPC: low-substituted hydroxypropyl cellulose
MN: D-mannitol
PVA: polyvinyl alcohol
S: D-sorbitol
pbw: part by weight, and
wt %: % by weight.

TABLE 2

| | | tablet properties | | | |
|---|---|---|---|---|---|
| | | immediately after the production | | after one week storage under humid conditions (40° C. and 75% RH) | |
| | tableting pressure (KN) | hardness (N) | disintegration time in oral cavity (seconds) | hardness (N) | disintegration time in oral cavity (seconds) |
| Example 1 | 7.5 | 42.1 | 13.8 | 46.1 | 14.8 |
| Example 2 | 7.5 | 51.5 | 17.1 | 58.0 | 19.4 |
| Example 3 | 5.0 | 54.9 | 15.1 | 70.2 | 13.8 |
| Example 4 | 5.0 | 49.8 | 16.6 | 64.2 | 20.7 |
| Example 5 | 5.0 | 53.4 | 17.7 | 68.1 | 21.8 |
| Example 6 | 5.0 | 57.9 | 19.3 | 72.3 | 24.2 |
| Example 7 | 5.0 | 59.1 | 20.5 | 74.3 | 25.5 |
| Comp. Ex. 1 | 7.5 | 53.8 | 25.9 | 73.8 | 52.1 |
| Comp. Ex. 2 | 5.0 | 59.6 | 21.3 | 75.5 | 30.5 |
| Comp. Ex. 3 | 5.0 | 60.8 | 29.3 | 99.7 | 70.1 | showed excellent disintegrability, but the disintegration time became longer after storage of the tablets under humidified conditions.

In Example 4 where the first D-sorbitol content in the D-mannitol comprised by the aqueous dispersion was 0.9% by weight or greater, and in Example 6 where the D-sorbitol content in the second D-mannitol to which the aqueous dispersion was added was 0.9% by weight or greater, both tablets immediately after the production as well as after storage under humidified conditions showed an excellent binding capability and disintegrability and were excellent in storage stability, similarly to the tablets obtained in Examples 5 and 7 in which the D-sorbitol contents in the D-mannitol comprised by granulated composites are similar to respective D-sorbitol contents in Examples 4 and 6.

Accordingly, even when the D-sorbitol content in the first D-mannitol comprised by the aqueous dispersion or the D-sorbitol content in the second D-mannitol to which the aqueous dispersion is added is more than 0.9% by weight, it is only necessary to make the D-sorbitol content in the D-mannitol comprised by the granulated composite 0.9% by weight or less.

According to the invention, orally disintegrating tablets excellent in binding capability and disintegrability and further excellent in storage stability under humidified conditions can be obtained by mixing the granulated composite with a drug and then tableting the resulting mixture.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:

1. A rapid release tablet, comprising a drug and a granulated composite comprising low-substituted hydroxypropyl cellulose having a degree of hydroxypropoxy substitution of from 5 to 16% by weight, a first D-mannitol and a second D-mannitol,
   wherein the granulated composite is not a physical mixture but has a modified surface by granulating while spraying a surface of the second D-mannitol with a homogenous mixture of the low-substituted hydroxypropyl cellulose and the first D-mannitol, an interior of the second D-mannitol not being surface-modified, and
   wherein the first D-mannitol and the second D-mannitol contain 0.81% by weight or less of D-sorbitol, and disintegration time of the tablet in an oral cavity is less than 30 seconds.

2. The rapid release tablet according to claim 1, wherein the homogenous mixture further comprises polyvinyl alcohol.

3. The rapid release tablet according to claim 1, wherein the first D-mannitol is present in the granulated composite in an amount of 5% to 50% by weight with respect to the total amount of D-mannitol.

* * * * *

UNITED STATES PATENT AND TRADEMARK OFFICE
CERTIFICATE OF CORRECTION

PATENT NO. : 11,723,872 B2
APPLICATION NO. : 16/601270
DATED : August 15, 2023
INVENTOR(S) : Hirama et al.

Page 1 of 1

It is certified that error appears in the above-identified patent and that said Letters Patent is hereby corrected as shown below:

In the Specification

Column 4, Line 9: Please correct "less than by weight" to read --less than 80% by weight--

Column 4, Line 44: Please correct "10 to 80 still" to read --10 to 80 μm, still--

Signed and Sealed this
Seventeenth Day of October, 2023

Katherine Kelly Vidal
*Director of the United States Patent and Trademark Office*